US010806582B2

(12) United States Patent
Newman et al.

(10) Patent No.: US 10,806,582 B2
(45) Date of Patent: Oct. 20, 2020

(54) PELVIC ANCHOR FOR PENILE PROSTHETIC IMPLANTS

(71) Applicant: MHN BIOTECH LLC, Chevy Chase, MD (US)

(72) Inventors: Howard S. Newman, Annapolis, MD (US); Arthur L. Burnett, Baltimore, MD (US); Marcel I. Horowitz, Chevy Chase, MD (US)

(73) Assignee: MHN BIOTECH LLC, Chevy Chase, MD (US)

( * ) Notice: Subject to any disclaimer, the term of this patent is extended or adjusted under 35 U.S.C. 154(b) by 105 days.

(21) Appl. No.: 16/144,557

(22) Filed: Sep. 27, 2018

(65) Prior Publication Data
US 2019/0099272 A1   Apr. 4, 2019

Related U.S. Application Data

(60) Provisional application No. 62/565,384, filed on Sep. 29, 2017.

(51) Int. Cl.
*A61F 2/26* (2006.01)
*A61F 2/00* (2006.01)
*A61B 17/04* (2006.01)

(52) U.S. Cl.
CPC .............. *A61F 2/26* (2013.01); *A61F 2/004* (2013.01); *A61B 17/0401* (2013.01); *A61F 2250/0003* (2013.01)

(58) Field of Classification Search
CPC ............... A61F 2/26; A61F 2/004; A61F 5/41
USPC ...................................... 600/38–40
See application file for complete search history.

(56) References Cited

U.S. PATENT DOCUMENTS

| 5,063,914 A | 11/1991 | Cowen |
| 2007/0049791 A1 | 3/2007 | Merade et al. |
| 2014/0343612 A1 | 11/2014 | Rezach et al. |

FOREIGN PATENT DOCUMENTS

WO   2017109729 A1   6/2017

OTHER PUBLICATIONS

International Search Report and Written Opinion dated Dec. 6, 2018 in PCT/US18/53138.

*Primary Examiner* — John P Lacyk
(74) *Attorney, Agent, or Firm* — Hogan Lovells US LLP

(57) ABSTRACT

Embodiments of the present disclosure include a system for anchoring implantable medical devices to bones. It includes an implantable medical device such as an inflatable penile prosthesis, a sliding edge clamp for anchoring at least partially around a bone, and a prosthesis receptacle coupled to the sliding edge clamp and extending outwardly and positioned to receive the prosthesis.

20 Claims, 13 Drawing Sheets

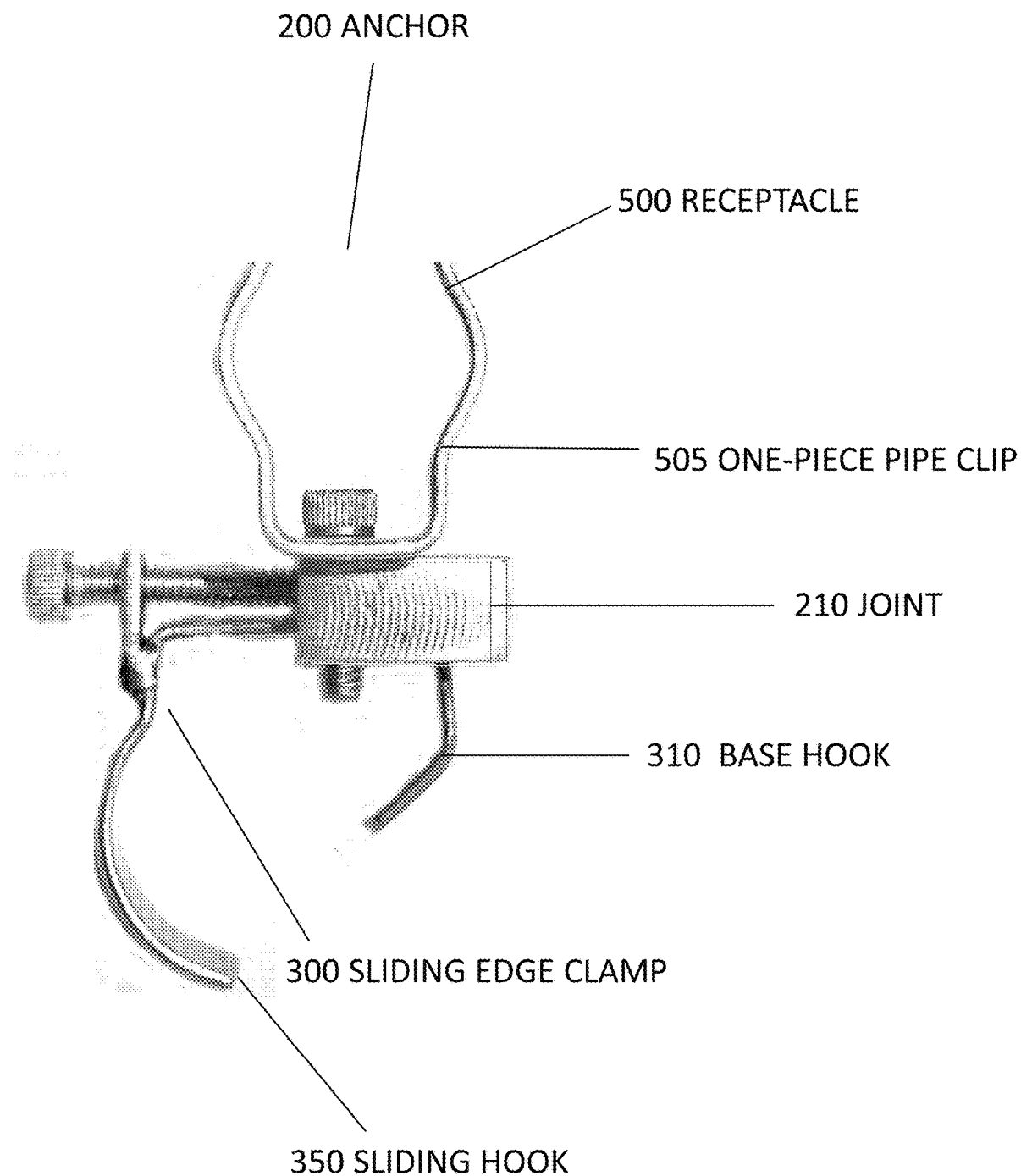

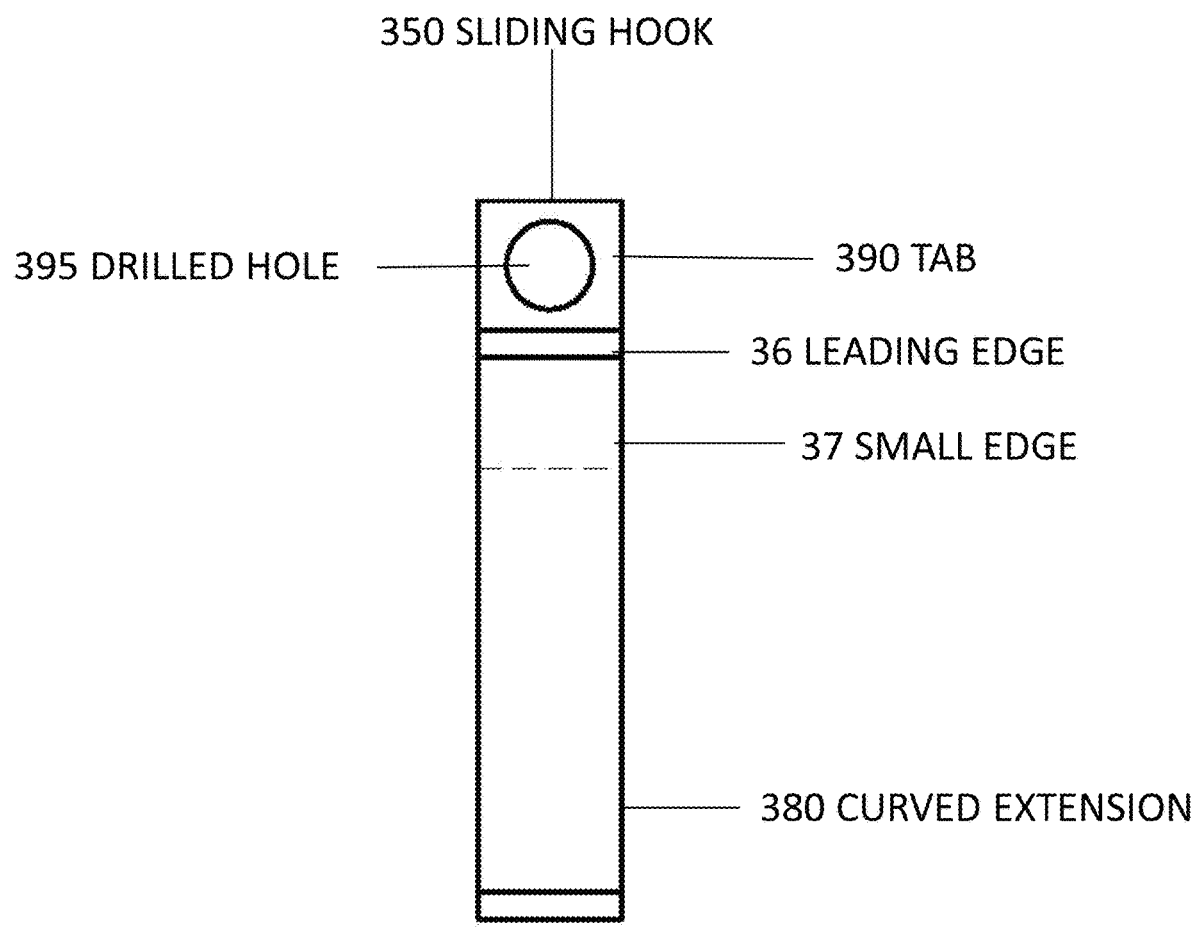

US 10,806,582 B2

PELVIC ANCHOR FOR PENILE PROSTHETIC IMPLANTS

CROSS-REFERENCE TO RELATED APPLICATIONS

This application claims priority to U.S. Provisional Application No. 62/565,384, filed Sep. 29, 2017, the contents of which are incorporated herein by reference.

FIELD OF THE INVENTION

The present disclosure relates to implanted medical devices. More particularly, the present disclosure relates to systems and methods for anchoring implanted medical devices, such as penile prostheses, to bones.

BACKGROUND OF THE INVENTION

Currently, clinicians are developing surgical procedures and devices to treat patients with severe penile defects or loss. Examples of such defects and loss can include congenital penile abnormalities (e.g., aphallia, micropenis, complex severe hypospadias, classic bladder exstrophy/epispadias complex, cloacal exstrophy), sexual differentiation disorders (i.e., ambiguous genitalia), penile trauma resulting in penile destruction, penectomy (e.g., as required for malignancy), and female-to-male gender reassignment.

These conditions may be addressed with major genital reconstructive procedures using local tissue or autogenous reconstruction (i.e., using tissue flaps) of a phallus (or penile allotransplantation). In these cases, a penile prosthesis is commonly inserted into the reconstructed penis to facilitate erection in patients without or with limited penile structures, such as in cases of the aforementioned penile trauma, penectomy, and female-to-male gender reassignment.

Penile prostheses are known as one option to treat erectile dysfunction. One such device includes two inflatable cylinders, a fluid reservoir, a pump and a reversing switch. The pump transfers fluid to and from the cylinders and the reservoir for cylinder inflation and deflation respectively, as set by the reversing switch. Each cylinder is comprised of an inflatable tube attached to a solid endcap. The endcap has a fill tube connection for transferring fluid to and from the inflatable tube. Each cylinder is implanted in each corpus cavernosa of an existing penis. The fluid reservoir is implanted in the abdomen. The pump and reversing switch are implanted in the scrotum. A fill tube connects the reservoir to the pump, and two fill tubes connect the pump to each endcap fill tube.

The inflatable cylinder endcaps typically anchor to the pelvis through intact corpora, which diverge forming the crura that anchor to the ischiopubic rami. Anchoring the prosthesis using existing corpora and crura tissue prevents the prosthesis from migrating from its intended position and possibly eroding through to the perineum when compressive loads are applied during intercourse. Indeed, any deviation of the prosthesis' intended position is problematic.

For patients without existing corpora, the penile prosthesis must be alternatively anchored to the pelvis. In the past, clinicians have anchored pelvic devices, such as organ supporting meshes, by suturing them to the periosteum tissue that encases the pubic bones, or, less commonly, by inserting screws directly into the pelvic bones. In suturing, sheathes are hand constructed using Gore-Tex or some other synthetic mesh material and hand sewn to the periosteum tissue that encases the pubic bones.

The implementation of such alternative anchoring is tedious, time consuming, and prone to withdrawal/dislodgement. Inserting screws directly into pelvic bones has its own sets of problems, including serious complications in some patients, such as infection, chronic pain and loosening of the screws.

What is needed is a device that safely and securely anchors penile prostheses close to and aligned with the ischiopubic rami without injury to the numerous blood vessels and nerves in the area; does not interfere with the pelvic structures such as the urethra; is not palpable by the patient or interfere with the patient sitting; can connect existing and future prosthesis designs; can be quickly attached by the surgeon to limit patient time under anesthesia; and has a long service life under the stress of patient activity.

SUMMARY OF THE INVENTION

Applicants recognized the problems noted above herein and conceived and developed embodiments of apparatus and methods, according to the present disclosure, for anchoring of implanted medical devices, such as penile protheses, to bones. Specifically, embodiments include a system and method for anchoring dual or single cylinder penile prostheses, with inflatable cylinders and solid endcaps with fill tubes, to the left and/or right medial inferior ramus of the ischium, which, with the inferior pubic ramus above it, forms the ischiopubic ramus. Additionally, the apparatus may be used to anchor other implanted medical devices to other bones.

In an embodiment, the device comprises a joint in communication with a prosthesis receptacle on one side and a sliding edge clamp on the other side and an inflatable penile prosthesis comprised of an inflatable tube distal and a solid endcap proximal. The prosthesis clamps in the receptacle, the receptacle attaches to the joint, the joint attaches to the sliding edge clamp, and the sliding edge clamp attaches to the bone, resulting in the prosthesis being attached to the bone.

Rivets, machine screws and welds may be used to attach the receptacle and sliding edge clamp to the joint. The device is kept small because there is little lateral room for a device to hold two inflatable cylinders in the location of a normal penis and not have the device protrude such that the patient can feel it. The device may be constructed from MRI-safe materials such as martensitic stainless steel, titanium, zirconia and polyetheretherketone (PEEK).

The joint may be comprised of a small, thin baseplate with a channel cut down the length of the baseplate's bottom. A U-shaped base hook, which forms one half of the sliding edge clamp, is fastened across and below the channel creating a slot for accepting a sliding hook which forms the other half of the sliding edge clamp. A drilled and tapped hole above the slot receives a screw which passes through a tab on the sliding hook and tightens the sliding hook against the bone which is located between it and the base hook. The baseplate may also have a protrusion, which extends out from one side. At least one prosthesis receptacle mounting hole, which may be tapped, is drilled through the baseplate to receive one or more rivets or screws for securing the receptacle to the joint. Left and right joints may be provided because baseplate's with protrusions are asymmetric.

Padding, such as polymethyl methacrylate (PMMA) bone cement, may be applied between the bone and the sliding edge clamp, thereby filling any free space between the sliding edge clamp and the bone to ensure that the sliding edge clamp remains in place with patient activity over time.

In an embodiment, the receptacle is in the form of a one-piece pipe clip which secures the endcap to the joint in a manor such that the prosthesis' cylinder lies close to and parallel with the medial ischiopubic ramus, with its proximal end lying along the medial inferior ramus of the ischium. The receptacle is wide enough to encompass the cylindrical portion of the endcap, such that the endcap will not wear and loosen from the clamp with patient activity over time. The bottom of the one-piece pipe clip is attached to a joint receptacle mounting hole by a screw or rivet allowing it to rotate 360° around the plane of the joint, thereby allowing a surgeon to align the prosthesis with the patient's anatomy. The one-piece pipe clip's inside diameter is slightly smaller than that of the endcap such that spring tension holds the endcap in place once the surgeon pushes the endcap into the one-piece pipe clip. Existing cylindrical penile prostheses may be anchored to bones using this device, with no modification required.

In another embodiment, the receptacle is in the form of a socket clamp which secures the endcap in the receptacle such that the prosthesis' cylinder lies close to and parallel with the medial ischiopubic ramus, with its proximal end lying along the medial inferior ramus of the ischium. The socket clamp is comprised of a thin wall pipe or truncated cone with an inside size and shape matching the outside size and shape of the endcap. A cutout may be placed at one end of the socket clamp to allow the fill tube to protrude through the socket clamp, thereby allowing the socket clamp to be long enough to encompass enough of the endcap such that the endcap will not wear and loosen with patient activity over time. The bottom of the socket clamp is attached to a joint receptacle mounting hole by a screw or rivet allowing it to rotate 360° around the plane of the joint, thereby allowing a surgeon to align the prosthesis with the patient's anatomy. A set screw, pipe clamp or clip may secure the endcap in the socket clamp. Existing cylindrical penile prostheses may be attached to the bones using this device, with no modification required.

In another embodiment, the receptacle is in the form of a pin clamp which is comprised of a machine screw passing through both a thin-walled pipe section washer and a hole drilled in the endcap. The washer's inside diameter matches the outside diameter of the endcap. A cutout may be placed at one end of the washer to allow a fill tube to protrude through the washer, allowing the washer to be long enough to encompass the cylindrical portion of the endcap such that the endcap will not wear and loosen with patient activity over time. The screw is then screwed into a joint receptacle mounting hole allowing the prosthesis to rotate 360° around the plane of the joint thereby allowing a surgeon to align the prosthesis with the patient's anatomy. The endcap hole may be predrilled for the machine screw to pass through. This embodiment requires modification of existing prostheses or future introduction of an updated prosthesis.

In another embodiment, the receptacle is in the form of an ear clamp which secures the endcap to the baseplate such that the prosthesis' cylinder lies close to and parallel with the medial ischiopubic ramus, with its proximal end lying along the medial inferior ramus of the ischium. The ear clamp is comprised of a thin wall cylinder with an inside diameter matching the outside diameter of the endcap. The ear clamp may have one or two tightening ears which lie parallel to the ischiopubic ramus. An offset crimping pliers is used to close the ears, thereby tightening the clamp about the prosthesis. The cylinder is wide enough to encompass the cylindrical portion of the endcap such that the endcap will not wear and loosen with patient activity over time. The bottom of the ear clamp is attached to a receptacle mounting hole by a screw or rivet allowing it to rotate 360° around the plane of the joint, thereby allowing a surgeon to align the prosthesis with the patient's anatomy. Existing cylindrical penile prostheses may be attached to bones using this device, with no modification required.

In another embodiment, the receptacle is in the form of a slotted O-clip, which secures the endcap such that the prosthesis' cylinder lies close to and parallel with the medial ischiopubic ramus, with its proximal end lying along the medial inferior ramus of the ischium. The slotted O-clip is comprised of a thin slotted coiled band with overlapping inside and outside ends. A hook is placed on the inside of the outside end to catch a slot on the outside of the inside end, thereby holding the band tightly closed. A tab is placed on the outside of the of the outside end. To tighten the slotted O-clip around the endcap, an offset tightening tool catches the tab and a slot in the inside end and squeezes them together. The slotted O-clip is wide enough to encompass the cylindrical portion of the endcap such that the endcap will not wear and loosen with patient activity over time. The bottom of the slotted O-clip is attached to a joint receptacle mounting hole by a screw or rivet allowing it to rotate 360° around the plane of the joint, thereby allowing a surgeon to align the prosthesis with the patient's anatomy. Existing cylindrical penile prostheses may be attached to the bones using this device, with no modification required.

In an embodiment, a method for surgically securing the prosthesis to a bone includes making an opening incision in a patient laterally across the ischiopubic arch and below the pubic symphysis, and exposing a small portions of the medial ischiopubic rami. Two sliding edge clamps and the prosthesis are then loosely fitted at each medial inferior ramus of the ischium and along the medial ischiopubic ramus to determine fit such that there is no interference with the structures situated behind, anterior to and posterior to the medial ischiopubic ramus. After the best fit is found, padding may be applied to the bone. Then, the sliding edge clamp is secured to the bone, the prosthesis is installed into the reconstructed penis, and the prosthesis is secured in the receptacle. Finally, a standard incision closing is performed.

BRIEF DESCRIPTION OF THE DRAWINGS

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

FIG. 2 is a top view of an embodiment of a pelvic anchor, in accordance with embodiments of the present disclosure;

FIG. 3C is a schematic front elevational view of an embodiment of a sliding hook of a sliding edge clamp, in accordance with embodiments of the present disclosure;

DETAILED DESCRIPTION OF THE INVENTION

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "an embodiment", "certain embodiments", or "other embodiments" of the present disclosure are not intended to be interpreted as excluding the existence of additional embodiments that also incorporate the recited features. Furthermore, reference to terms such as "above", "below", "upper", "lower", "side", "front", "back", or other terms regarding orientation or direction are made with reference to the illustrated embodiments and are not intended to be limiting or exclude other orientations or directions.

Embodiments of the present disclosure relate to systems and methods involving implantable medical devices, such as dual inflatable cylinder penile prostheses, which may be inserted into surgically reconstructed penises to facilitate erections. For example, one or more embodiments are directed towards a system and method for a surgeon to firmly anchor the proximal ends of the dual inflatable cylinders of a dual cylinder penile prosthesis to the pelvic medial ischiopubic rami, each ramus comprised of an inferior ramus of the ischium and an inferior pubic ramus. Anchoring permits the transfer of axial loads from the penile prosthesis to the pelvis during intercourse, thereby preventing the prosthesis from entering the perineum or causing other tissue damage through its movement.

A penile prosthesis may be used in penile reconstruction for males and for female transgender reconstruction surgery. Since ischiopubic rami size, irregular shape and orientation vary between males and females and among each gender, an anchor for the inflatable cylinders and their method of installations by the surgeon requires adjustable apparatus for fitting different patients with different prostheses and an emplacement position easily accessible to the surgeon.

Figure 1A:
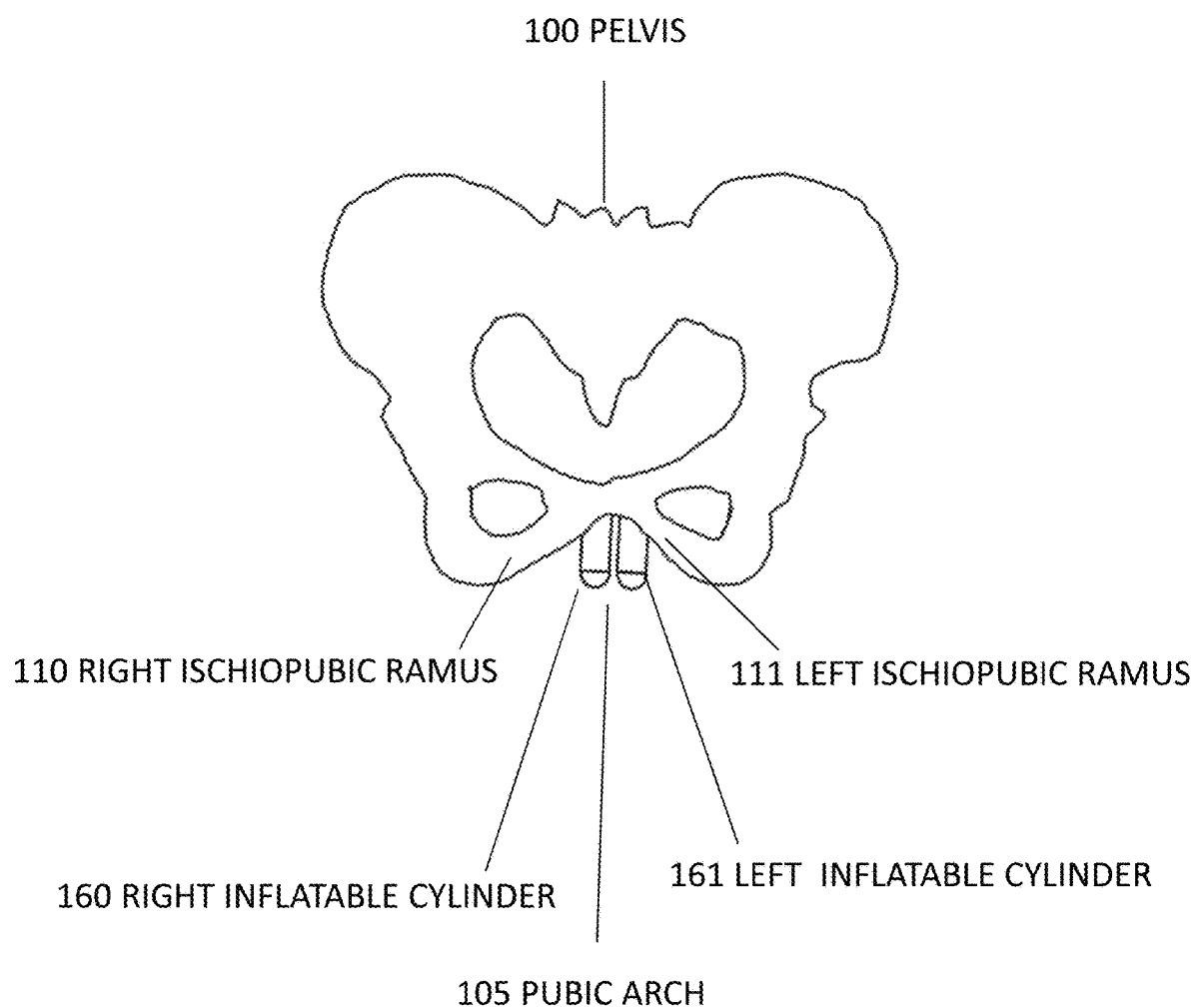
FIG. 1A is a front elevational schematic view of an embodiment of a pelvis having a dual cylinder penile implant anchored to the left and right medial ischiopubic ramus, in accordance with embodiments of the present disclosure.

FIG. 1A illustrate a frontal view of an embodiment of a pelvis 100 with dual inflatable cylinders 160, 161 of a dual inflatable cylinder penile prosthesis system anchored thereon. The dual cylinders 160, 161 emerge from the pubic arch 105 formed by the right and left ischiopubic rami 110, 111. While the illustrated embodiment includes a pair of cylinders 160, 161, there may be more or fewer cylinders. In addition, the cylinders may be positioned at other locations. Other medical devices, such as bladder or uterus support meshes, may also be anchored to the pelvis 100 in the same manner as for the penile cylinders 160, 161. Moreover, medical implants may similarly be anchored to other bones.

Figure 1B:
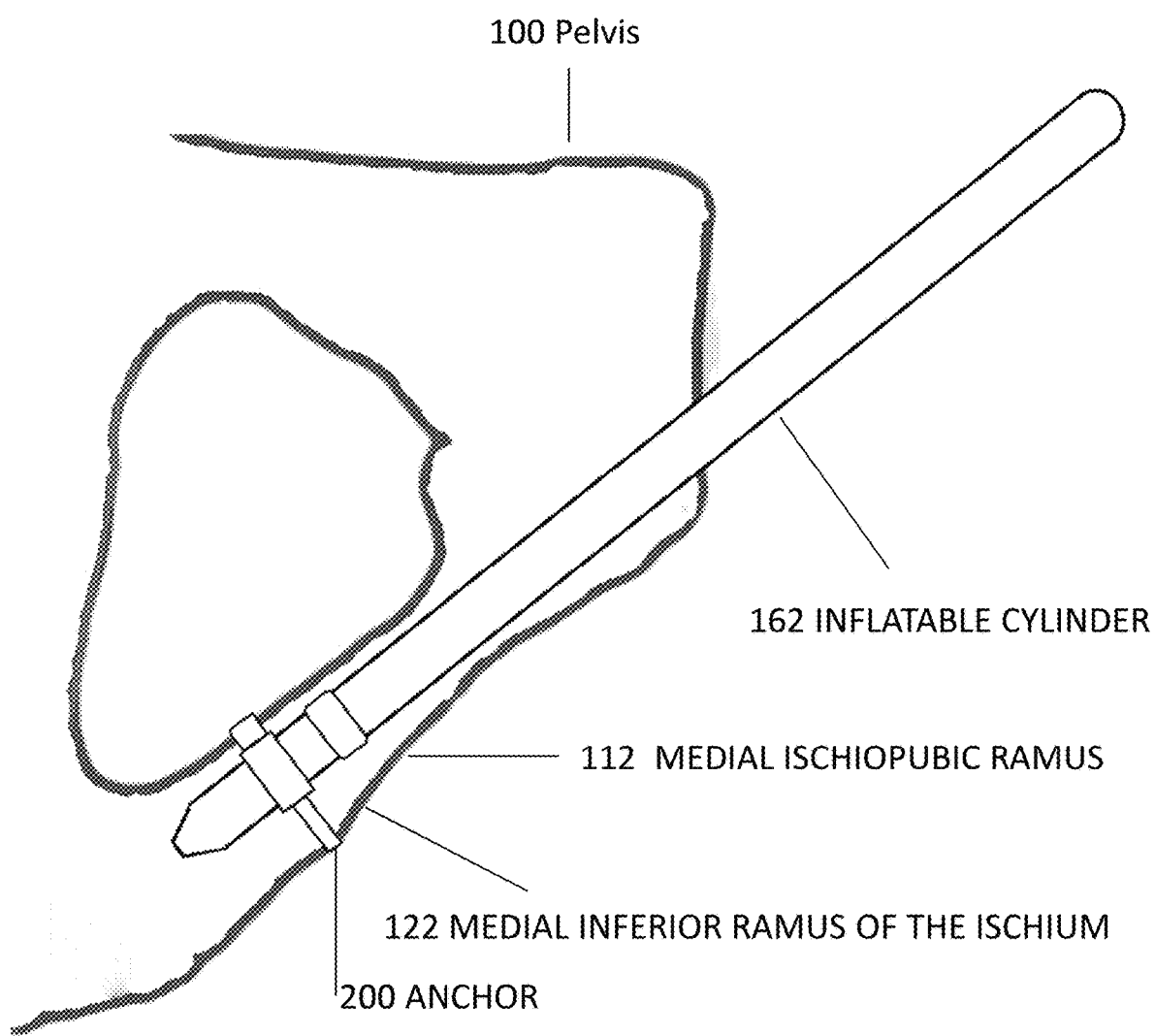
FIG. 1B is a medial side elevation schematic view of an embodiment of one cylinder of a dual cylinder penile prosthesis attached to the left medial inferior ramus of the ischium, in accordance with embodiments of the present disclosure.

FIG. 1B illustrates an embodiment of a medial ischiopubic ramus 112 with an inflatable cylinder 162 secured by an anchor 200 to the medial inferior ramus of the ischium 122. The inflatable cylinder 162 may be secured by the anchor 200 close to and aligned with the medial ischiopubic rami 112 of the pelvis 100. The proximal end of cylinder 162 may be connected by the anchor 200 to the medial inferior ramus of the ischium 122 and may have its distal end lie along the medial ischiopubic rami 112 Due the anatomy of the normal penis, anchoring at this position more closely mimics cosmetically the normal penis location, and does not interfere with structures of the pelvis. Further, this position is easily accessed surgically.

FIG. 2 illustrates an embodiment of an anchor 200. The anchor is comprised of a joint 210 with a sliding edge clamp 300 in communication with one side of a joint 210, and a receptacle 500, in the form of a one-piece pipe clip 505, in communication with the other side of the joint 210. The receptacle 500 clamps a prosthesis cylinder to the joint 210 and the sliding edge clamp 300 clamps the joint 210, with its attached prosthesis cylinder, to the medial inferior ramus of the ischium. The sliding edge clamp 300 is comprised of a base hook 310 working in conjunction with a sliding hook 350. The device is small because there is little lateral room in the pubic arch for two devices and two inflatable cylinders 160, 161. Additionally, the device must not protrude behind, anterior to or posterior to the pubic arch such that it does not interfere with pelvic structures, is not palpable by the patient, and does not interfere with the patient sitting.

Moreover, the receptacle 500 may enable movement in one or more planes, such as rotational planes, with respect to the joint 210 to enable alignment of the prosthesis with the reconstruction. Furthermore, the receptacle 500 may be attached to a receptacle mounting hole in the joint 210. In this manner, the prosthesis cylinder may be securely anchored to the medial inferior ramus of the ischium. This also allows the prosthesis cylinders to be aligned with the ischiopubic rami to reduce the likelihood of movement and damage to surrounding tissues, to be quickly attached by the surgeon, and to have a long service life under the stresses caused by patient activity.

Additionally, the components described herein with reference to the receptacle 500 may be formed from biocompatible, MRI-safe materials, such as stainless steel (e.g., 316L), titanium, plastics (e.g., polyetheretherketone (PEEK)), zirconia, or combinations thereof. In certain embodiments, receptacle 500 may be constructed by 3-D printing or molding.

Figure 3A:
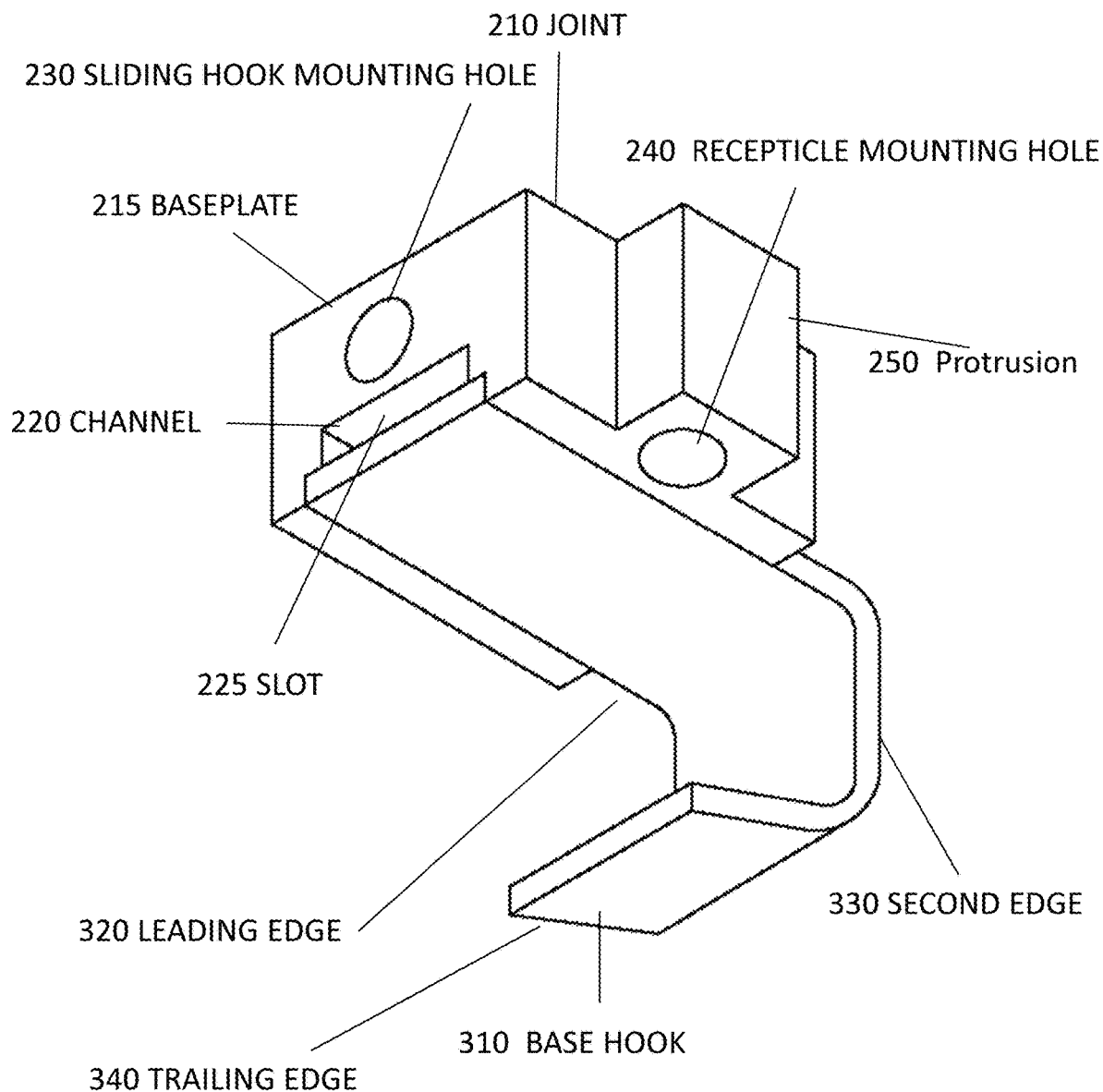
FIG. 3A is a bottom isometric view of a joint with a base hook of a sliding edge clamp attached, in accordance with embodiments of the present disclosure.
Figure 3B:
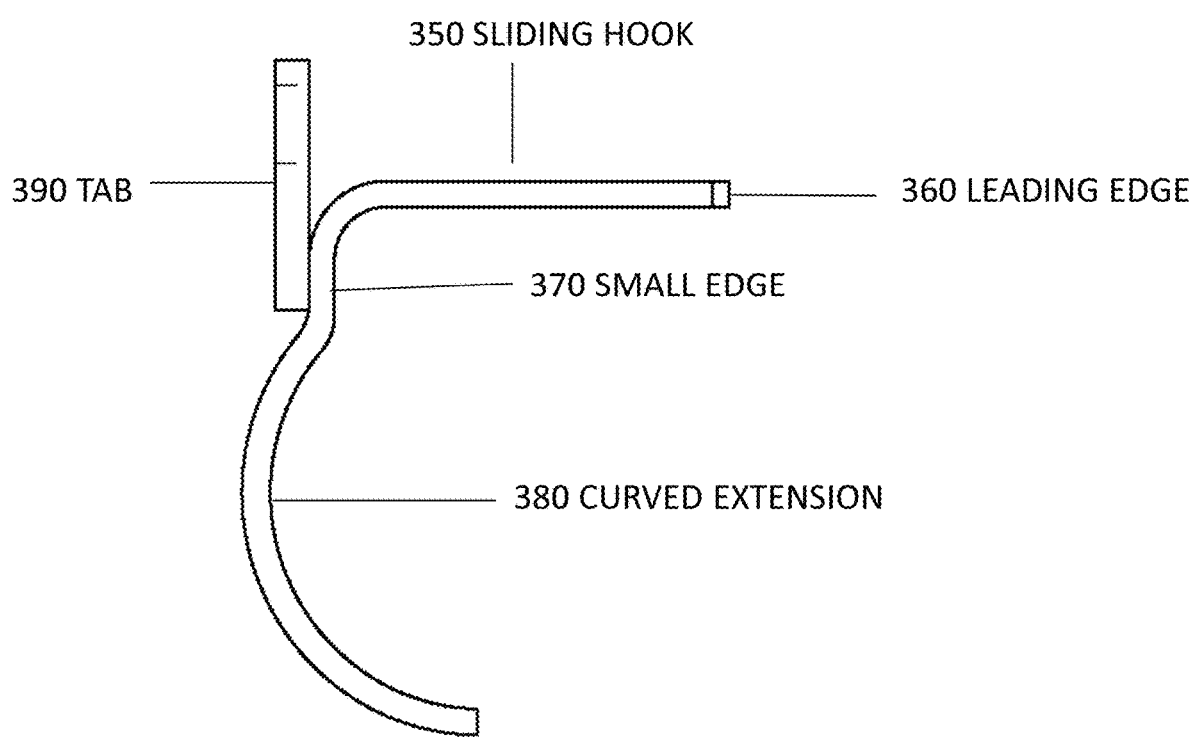
FIG. 3B is a schematic side elevational view of an embodiment of a sliding hook of a sliding edge clamp, in accordance with embodiments of the present disclosure.

FIG. 3A illustrates a bottom isometric view of an embodiment of a joint 210 which has a base hook 310 of a sliding edge clamp firmly attached. FIG. 3B illustrates a side elevation view of a sliding hook 350 of the sliding edge clamp, and FIG. 3C illustrates a front elevation view of the sliding hook 350. The base hook 310 and the sliding hook 350 form the sliding edge clamp.

The joint 210 may be a small, thin baseplate 215 with a channel 220 cut down the length of the bottom. For example, the joint may be 0.5 inches long by 0.2 inches thick. The channel may be covered by the base hook's 310 leading edge 320, thereby forming a void or slot 225 for receiving the leading edge 360 of the sliding hook 350. The baseplate may also have a protrusion, which extends out from one side.

The base hook 310, which may be looped around at least a portion of the posterior medial inferior ramus of the ischium has a leading edge 320 which forms the top of the slot 225, a second edge 330 bent at 90 degrees to the leading edge, and a trailing edge 340 which may be bent at 120 degrees to the second edge 330. The base hook 310 may extend beyond the joint 210 to minimize the joint's 210 impact on tissues posterior to the bone. This extension beyond the joint 210 may be minimal, such as 0.1 inches.

A sliding hook mounting hole 230 is drilled and tapped above and parallel to the slot 225 to accept a screw which tightens the sliding hook 350 against the base hook 310 with the bone in between, thereby clamping the joint 210 to the bone. At least one prosthesis receptacle mounting hole 240, which may be tapped, is drilled through the baseplate 215 to receive one or more rivets or screws for securing the receptacle to the joint. Left and right joints 210 may be provided for baseplates 215 with protrusions 250 due to their asymmetry.

The sliding hook 350, which is looped around at least a portion of the anterior medial inferior ramus of the ischium has a leading edge 360 at least as long as the bone's width and configured to enter the slot 225 and extend into its void; a small edge 370 bent at 90 degrees to the leading edge and configured to accept a tab 390; and a curved extension 380 to the small edge 370 whose radius is sized to catch an edge or side of a bone.

The tab 390 is attached to the outside of the sliding hook's 350 small edge 370. It has a drill hole 395 in its middle to match the sliding hook mounting hole 230 in the joint 210. A machine screw (not shown), which is at least as long as the leading edge 360 of the sliding hook 350, is passed through the drilled hole 395 in the tab 390 and screwed and tightened into the joint's 210 sliding hook mounting hole 230.

In certain embodiments, the bone may be padded, for example with a bone cement such as polymethyl methacrylate (PMMA) or a light sensitive curing material such as a resin matrix, to equally transfer hook 310, 350 pressure to the inferior ramus of the ischium. The padding material may be mixed in the operating room and applied while still malleable. Applying the sliding edge clamp at this time may result in a firm connection to the bone when the padding is fully set, thereby distributing the hook's 310, 350 pressure more evenly over the inferior ramus of the ischium's uneven bone structure. This reduces the likelihood of movement during installation and/or operation and reduces pressure on ridges in the bone structure.

The base hook 310 and the sliding hook 350 may be made from semi-rigid materials, such as 20 gauge 316L stainless steel. Tightening the semi-rigid material against the bone may cause the hooks 310, 350 to slightly deform thereby conforming to the bone contours for a better fit. Additionally, the second edge 330 and the trailing edge 340 of the base hook 310 and the curved extension 380 of the sliding hook 350 may have one or more friction surfaces, such a knurling, applied to distribute the hook's pressure more evenly over the inferior ramus of the ischium's uneven bone structure, reducing the likelihood of movement during installation and/or operation and reducing pressure on ridges in the bone structure.

As shown in FIG. 2, the sliding hook 350 is larger than the base hook 310 to account for the different size and shape of the inferior ramus of the ischium in different patients. Moreover, the sliding hook 350 may come in different lengths and have different curved extension 380 radii to enable a universal or semi-universal coupling to a variety of patients having different sized and shaped inferior rami of the ischium.

The components described with reference to the sliding edge clamp 300 and the joint 210 may be formed from biocompatible, MRI-safe materials, such as stainless steel (e.g., 316L), titanium, plastics (e.g., polyetheretherketone (PEEK)), zirconia, or combinations thereof. In certain embodiments, the joint 210 and the base hook 310 of the sliding edge clamp 300 may be constructed as a single piece, such as by 3-D printing or molding.

Sliding edge clamps have the advantage of being able to be tightened across a wide range of bone shapes and sizes by hooking around at least a portion of either a bone edge or a bone side without the need for the surgeon to completely expose the bone or place a foreign object in the bone. Using a sliding edge clamps to tightly anchor cylinders close to and aligned with the medial ischiopubic rami mimics the location of the penis. It also gives the surgeon quick, easy access to a sturdy anchoring point which requires minimum exposure of the rami, thereby minimizing the chance of surgical injury or blockage to the numerous structures in the area. As a result, patient time under anesthesia is decreased as compared to existing methods.

Other methods of tightening the sliding edge clamp against the inferior ramus of the ischium may be used, such as a ratchet ramp and a rack and pawl device. However, placing a tab on the sliding hook and using an easily accessible screw to tighten it into the joint may require the least surgery for placing and tightening of the sliding edge clamp.

Figure 4:
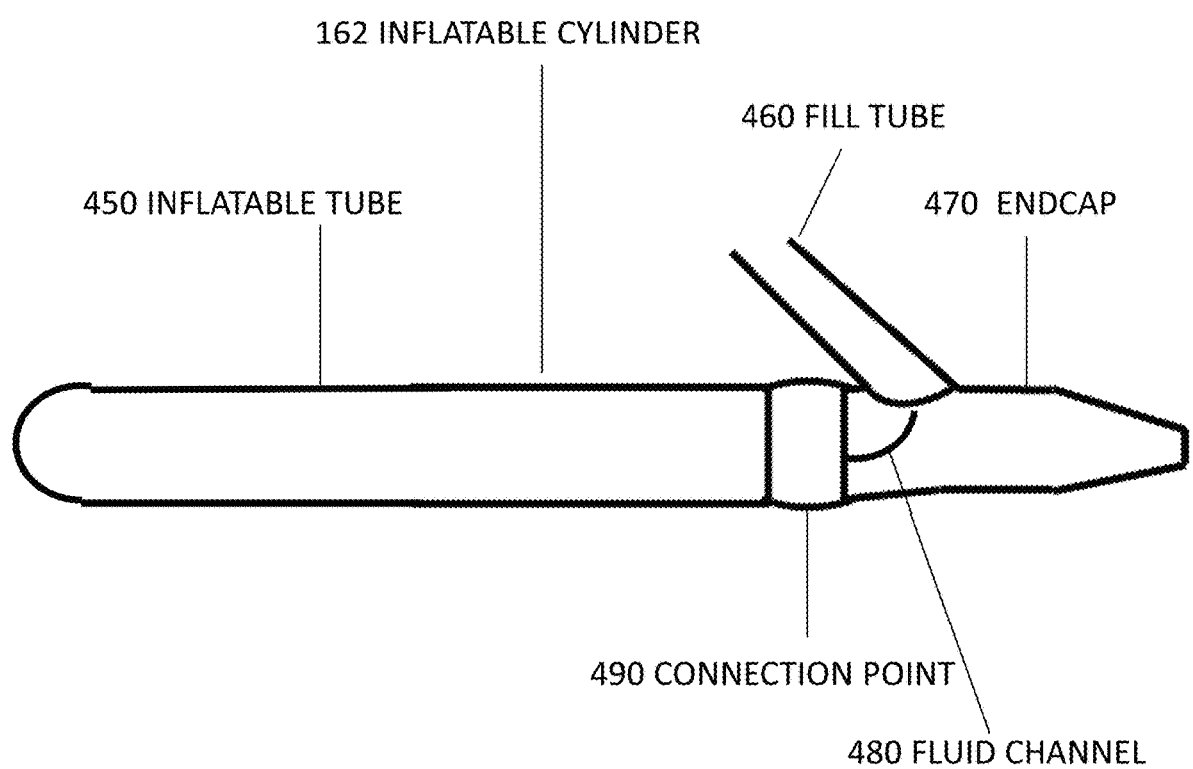
FIG. 4 is a schematic side elevational view of an embodiment of an inflatable penile prosthesis cylinder, in accordance with embodiments of the present disclosure.

FIG. 4 illustrates the front elevation of a penile prosthesis inflatable cylinder 162. In the illustrated embodiment, the cylinder 162 includes an inflatable tube 450 at its distal end and a solid endcap 470 at its proximal end. The inflatable tube 450 is attached over the endcap 470 at a connection point 490. A fluid fill tube 460 is attached to the endcap 470, and a small fluid channel 480 in the endcap 470 provides a path for fluid to flow from the fill tube 460 to the inflatable tube 450. The endcap 470 provides solid material to interact with a receptacle to thereby secure the cylinder to a joint. The proximal endcap 470 may be any reasonable shape and embodiments of the present disclosure are not intended to be limiting to cylindrical or cone-shaped arrangements.

Figure 5A:
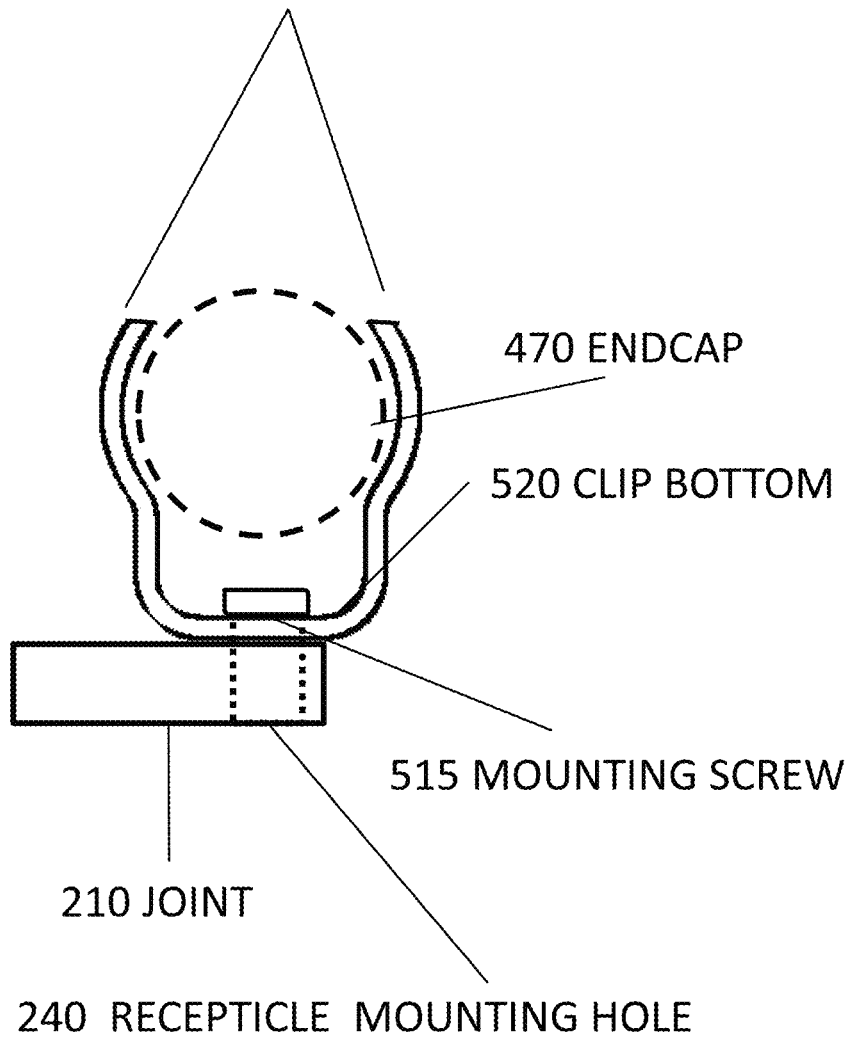
FIG. 5A is a side elevational schematic view of an embodiment of a one-piece pipe clip receptacle containing an endcap, in accordance with embodiments of the present disclosure.
Figure 5B:
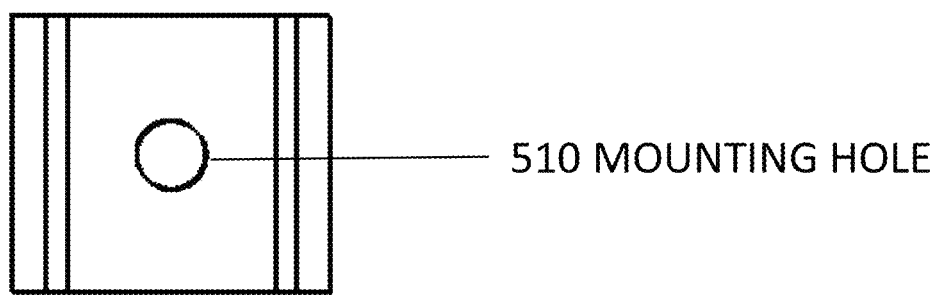
FIG. 5B is a top schematic view of an embodiment of a one-piece pipe clip receptacle, in accordance with embodiments of the present disclosure.

FIG. 5A and FIG. 5B illustrate an embodiment of the receptacle in the form of a one-piece pipe clip. FIG. 5A illustrates the one-piece pipe clip's side elevation view, with the endcap 470 also seen as a side elevation view, namely as a circle. FIG. 5B illustrates the one-piece pipe clip top view. The one-piece pipe clip may secure the endcap 470 to the joint 210 in a manner such that the prosthesis' cylinder lies close to and parallel with the medial ischiopubic ramus, with its proximal end lying along the medial inferior ramus of the ischium.

The one-piece pipe clip is wide enough to encompass the endcap 470 such that it will not wear or loosen from the one-piece pipe clip with patient activity over time. The one-piece pipe clip's bottom 520 may be attached to the joint receptacle mounting hole 240 by a mounting screw 515 or rivet running through a mounting hole 510, thereby allowing it to rotate 360° around the plane of the joint 210. This also allows the surgeon to place the prosthesis cylinder in a position that best aligns it with the patient's anatomy.

The pipe clip sides 530 may be partially rounded to a radius slightly smaller than that of the endcap 470, which may have a 0.4-inch radius. Once the surgeon pushes the endcap 470 into the one-piece pipe clip, spring tension holds the endcap 470 in place. This embodiment does not require any modification to existing cylindrical penile prostheses for attachment to the joint 210.

Figure 6:
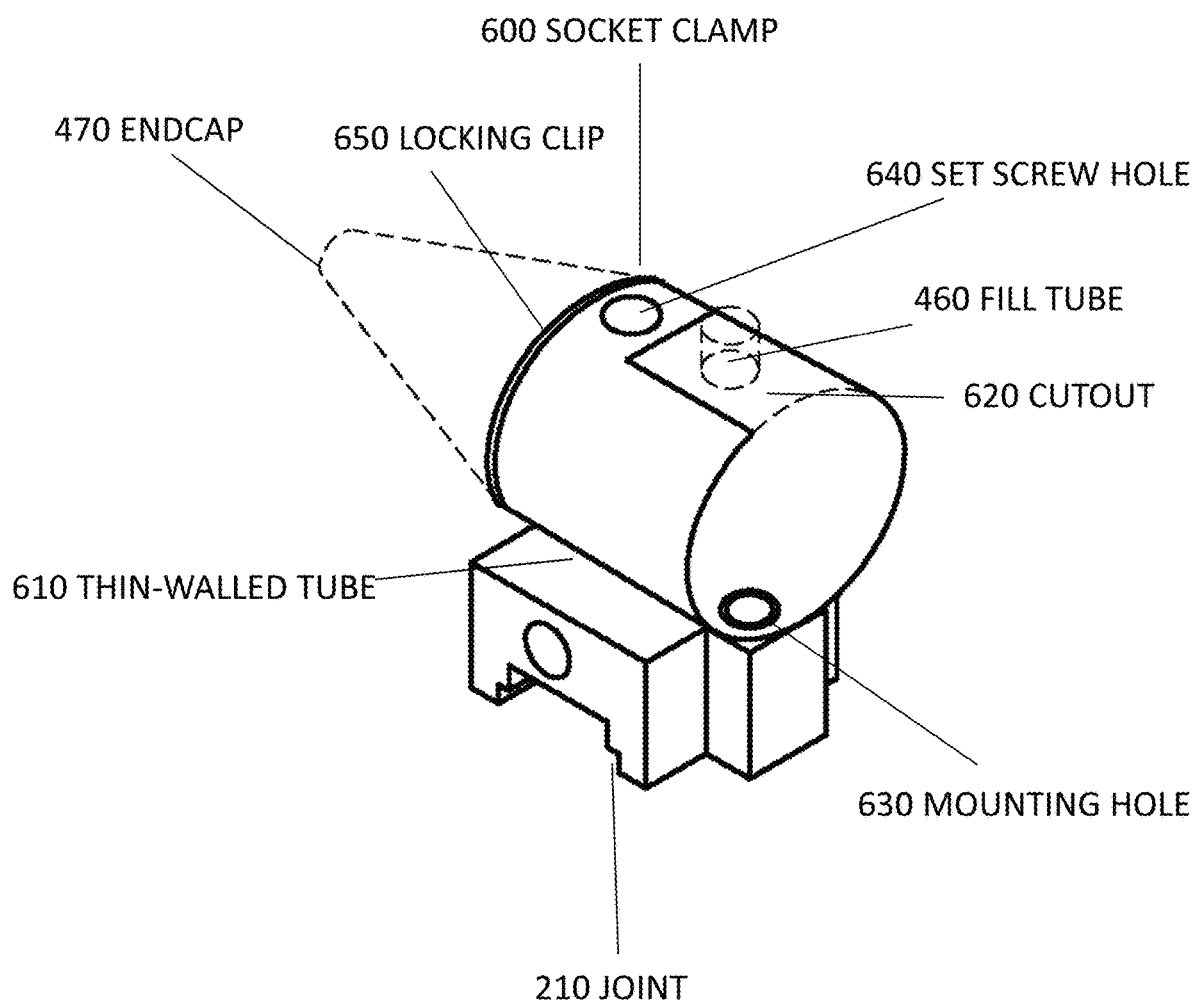
FIG. 6 is an isometric view of an embodiment of a socket clamp receptacle attached to a joint and containing an endcap, in accordance with embodiments of the present disclosure.

Another embodiment of the receptacle is in the form of a socket clamp 600, as illustrated in FIG. 6. The socket clamp secures the endcap 470 in a manner such that the prosthesis' cylinder lies close to and parallel with the medial ischiopubic ramus with its proximal end lying along the medial inferior ramus of the ischium. The socket clamp may be comprised of a thin-walled tube 610, which may be round or cone shaped, and who's inside size and shape matches the outside size and shape of the endcap 470. A cutout 620 may be placed at one end of the tube 610 to allow room for the prosthesis fill tube 460 to be encompassed by the tube 610, which provides for a longer tube 610 length. The tube 610 is long enough to encompass the cylindrical portion of the endcap 470 such that the endcap 470 will not wear and loosen with patient activity over. Drain holes (not shown) may be placed in the tube 610 to prevent fluid buildup after implantation.

The socket clamp 600 may be attached to the joint 210 by a screw or rivet running through a mounting hole 630, thereby allowing it to rotate 360° around the plane of the joint 210. This allows the surgeon to place the prosthesis cylinder across joint 210 such that it best aligns with the patient's anatomy. One or more set screws (not shown) placed in one or more drilled and tapped set screw holes 640 may secure the endcap 470 in the socket clamp 600. Additionally, a locking clip, such as a thin hose clamp, may be placed on the endcap in place of the set screw to hold the endcap in place. This embodiment does not require any modification to existing cylindrical penile prostheses for attachment to the joint 210.

Figure 7:
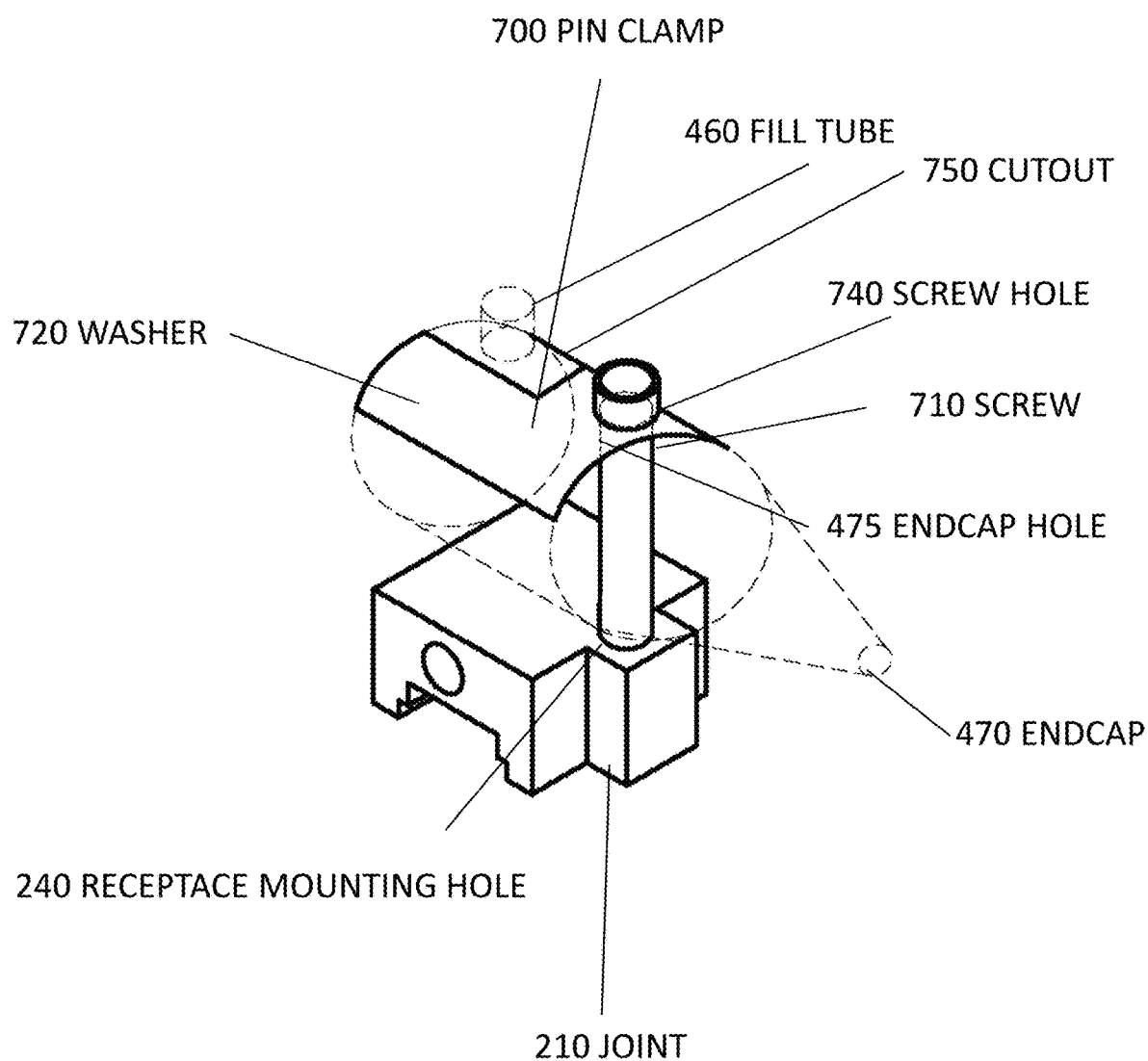
FIG. 7 is an isometric schematic view of an embodiment of a pin clamp receptacle attached to joint and containing an endcap, in accordance with embodiments of the present disclosure.

Another embodiment of the prosthesis receptacle is in the form of a pin clamp 700 which is comprised of a screw 710 and a semi cylindrical washer 720, as shown in FIG. 7. A machine screw 710 is passed through the washer 720 and a hole 475 drilled in the endcap 470 and screwed into the receptacle mounting hole 240, allowing the prosthesis cylinder to rotate 360° around the plane of the joint 210 thereby allowing the surgeon to place the prosthesis across joint such that it best aligns with the patient's anatomy. The washer is comprised of a thin-walled pipe section whose inside diameter matches the outside diameter of the endcap 470. A cutout 750 may be placed at one end of the washer 720 to allow room for the prosthesis fill tube 460 to be encompassed by the washer 720, which provides for a longer washer 720. The washer 720 is long enough to encompass the cylindrical portion of the endcap 470 such that the endcap 470 will not wear and loosen with patient activity over. A hole 475 may be predrilled in an existing endcap for the screw 710 to pass through. This embodiment requires modification of existing prostheses or the introduction of an updated prosthesis containing a hole 475 to receive the screw 710.

Figure 8:
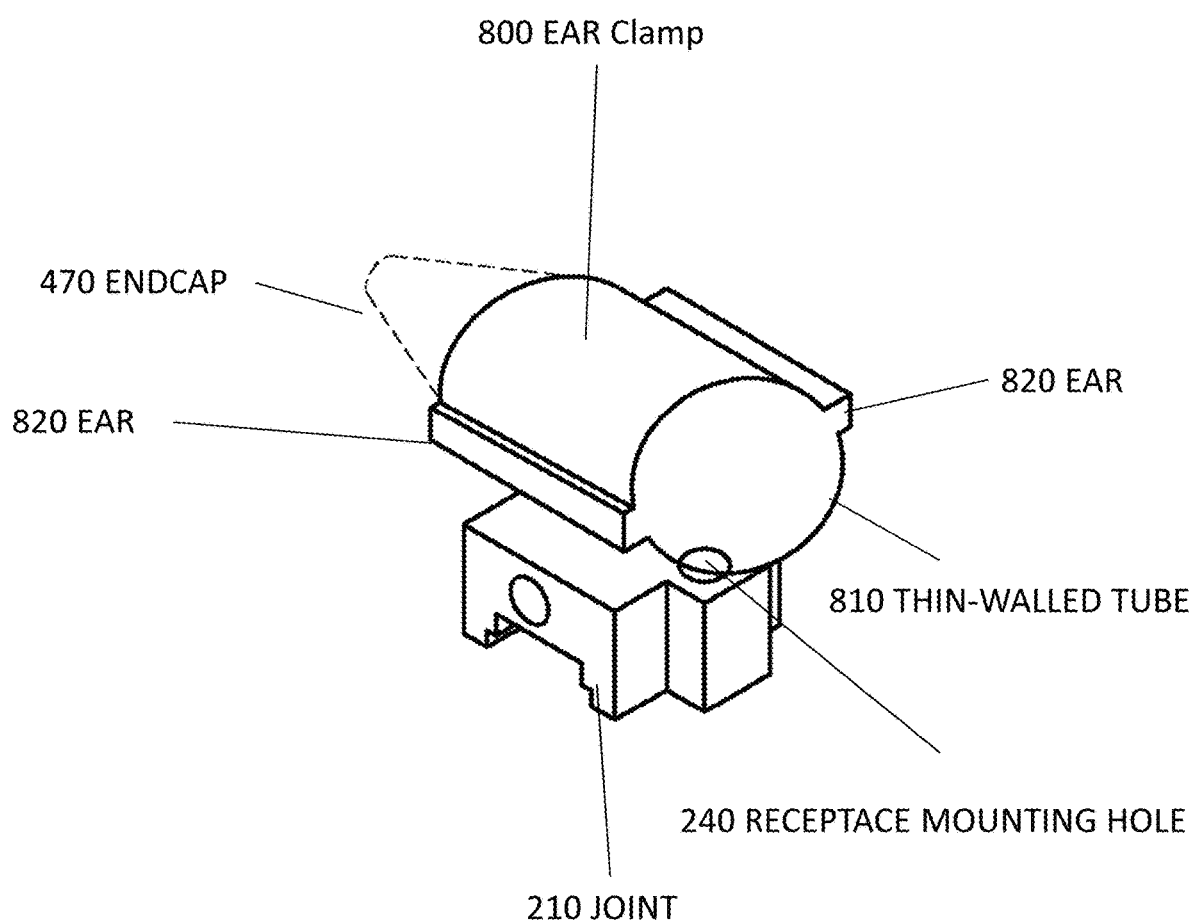
FIG. 8 is an isometric schematic view of an embodiment of an ear clip receptacle, in accordance with embodiments of the present disclosure.

In another embodiment, illustrated in FIG. 8, the receptacle may be in the form of an ear clamp 800 which secures the endcap to the joint 210 such that the prosthesis' cylinder lies close to and parallel with the medial ischiopubic ramus, with its proximal end lying along the medial inferior ramus of the ischium. The ear clamp 800 is comprised of a thin wall tube 810 with an inside diameter matching the outside diameter of the endcap 470. The ear clamp may have one or two tightening ears 820 which lie parallel to the ischiopubic ramus. An offset crimping pliers (not shown) is used to close the ears 820, thereby tightening the ear clamp 800 about the endcap 470. The tube 810 is wide enough to encompass the cylindrical portion of the endcap 470 such that the endcap 470 will not wear and loosen with patient activity over time. The bottom of the ear clamp 800 is attached to the receptacle mounting hole 240 by a screw or rivet allowing it to rotate 360° around the plane of the joint, thereby allowing a surgeon to align the prosthesis with the patient's anatomy. Existing cylindrical penile prostheses may be attached to bones using this device, with no modification required.

Figure 9A:
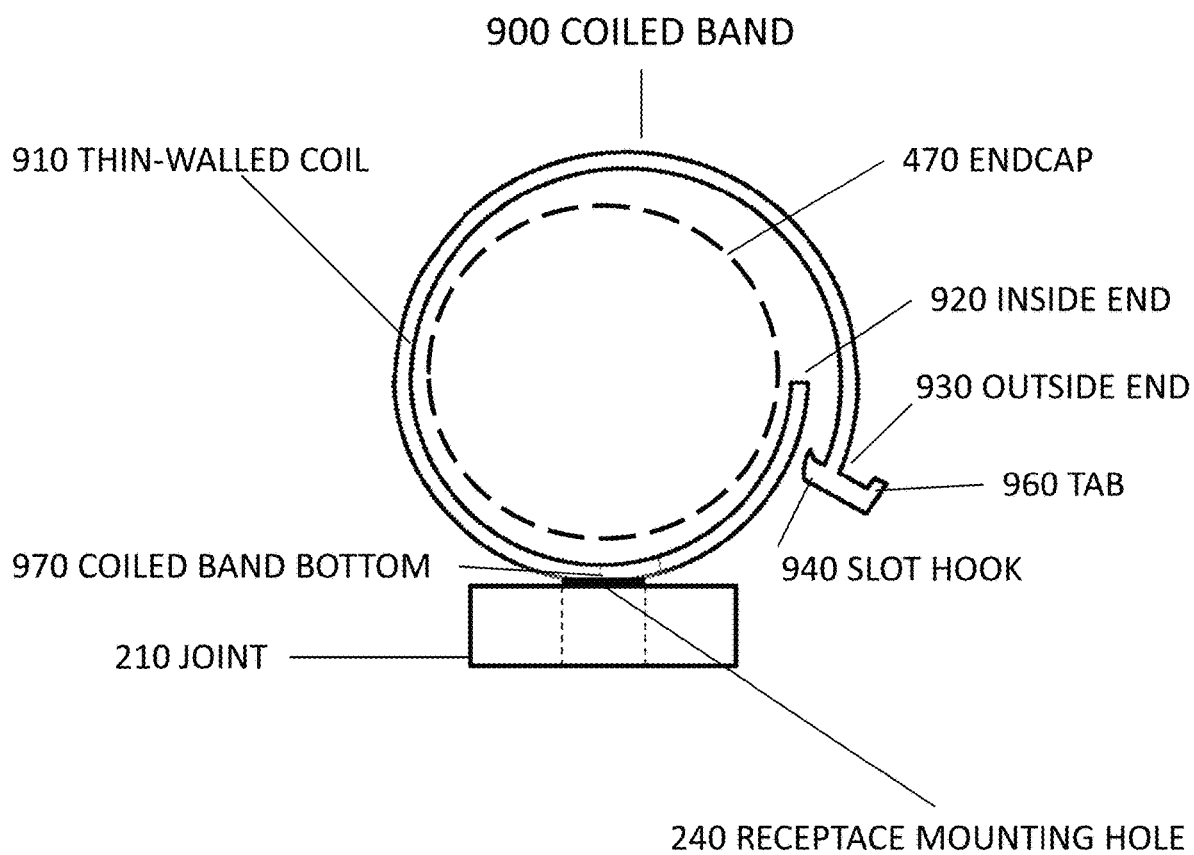
FIG. 9A is a side elevational schematic view of an embodiment of a slotted O-clip receptacle, in accordance with embodiments of the present disclosure.
Figure 9B:
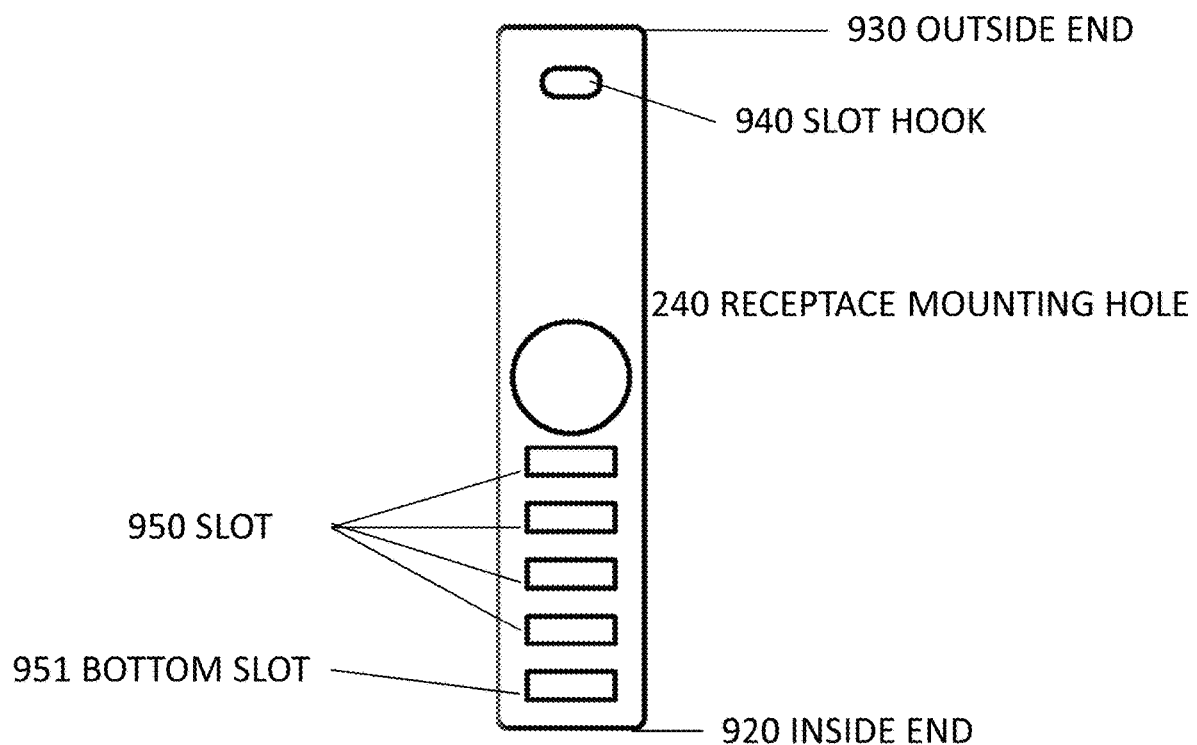
FIG. 9B is a top schematic view of an embodiment of an uncoiled slotted O-clip receptacle, in accordance with embodiments of the present disclosure.

In another embodiment, illustrated in FIG. 9A and FIG. 9B, the receptacle may be in the form of a slotted O-clip. FIG. 9A illustrates a side elevational view of the slotted O-clip placed around and an endcap 470, with the endcap 470 also seen in a side view. As shown, the slotted O-clip is in the form of a coiled band 900. FIG. 9B illustrates a top view of the coiled band 900 unwound and lying flat. The coiled band 900 secures the endcap 470 such that the prosthesis' cylinder lies close to and parallel with the medial ischiopubic ramus, with its proximal end lying along the medial inferior ramus of the ischium. The coiled band 900 is comprised of a thin coil 910 with an inside end 920 and an outside end 930. The inside end 920 overlaps with the outside end 930. A slot hook 940 placed on the inside of the outside end 930 catches a slot 950 on the outside of the inside end 920, thereby holding the coil 910 closed. There may be more slots 950, and of a different size and shape than shown in the illustration. A tab 960 is placed on the outside of the of the outside end 930. To tighten the coiled band 900 around the endcap 470, an offset tightening tool (not shown) catches the tab 960 and the bottom slot 951 in the inside end and a handle on the tool squeezes the tab 960 towards the bottom slot 951, thereby tightening the coiled band 900 around the endcap 470.

The coiled band 900 is wide enough to encompass the cylindrical portion of the endcap 470 behind the fill tube, such that the endcap 470 may not wear and loosen with patient activity over time. The coiled band bottom 870 is attached to the joint receptacle mounting hole 240 by a screw or rivet allowing it to rotate 360° around the plane of the joint, thereby allowing a surgeon to align the prosthesis with the patient's anatomy. Existing cylindrical penile prostheses may be attached to the bones using this device, with no modification required.

Inflatable cylinders of a penile prosthesis, such as a dual cylinder penile prosthesis system, may be surgically secured to each medial inferior ramus of the ischium. The procedure itself occurs at a final or near final stage of serial reconstructive procedures for a female-to-male gender reassignment surgery or a surgery for a congenitally deformed male (i.e., exstrophy). Thus, the neophallus and neoscrotum have been previously created. Proceeding at this stage for placement of the pelvic anchor and prosthesis, the surgeon positions the patient in dorsal lithotomy and standardly preps and drapes. The genital area is surgically exposed with an opening incision which may be made in the midline beneath the penoscrotal reconstruction and anterior to the anus, which provides bilateral access to the ischiopubic rami. Dissection continues on one lateral side then to the other, on each side exposing the ramus surgically and then placing a sliding edge clamp loosely over each medial inferior ramus of the ischium.

Measurement lengths are determined, and the appropriately sized cylinders are then brought to the operative stage and aligned with the proximal end loosely positioned with the sliding edge clamps. After that is done, the surgeon proceeds with insertion of the penile prosthesis. The anatomical course surgically developed as needed for the cylinders of the penile prosthesis routed into the neophallus distally and to the location of the sliding edge clamps proximally.

Padding material may then be applied over the bone at this time. The sliding edge clamp is then tightened over the bone and the endcap is inserted into receptacle and tightened therein. Thereafter, the fluid reservoir is inserted in the abdominal area with a secondary incision, filled with sterile fluid, and all fill tubing attachments are made subcutaneously. Standard wound closure is then performed with surgical closure.

The foregoing disclosure and description of the disclosed embodiments is illustrative and explanatory of the embodiments of the invention. Various changes in the details of the illustrated embodiments can be made within the scope of the appended claims without departing from the true spirit of the disclosure. The embodiments of the present disclosure should only be limited by the following claims and their legal equivalents.

The invention claimed is:

1. A system for anchoring prostheses to bones comprising:
a receptacle for holding at least one prosthesis; and
a sliding edge clamp for anchoring the receptacle to at least one bone, the sliding edge clamp hooking at least partially around the bone without penetrating it; and
a joint coupling the receptacle to the sliding edge clamp, the joint comprising at least one receptacle mounting hole for connecting the receptacle to the joint.

2. The system of claim 1, wherein the prosthesis comprises a cylindrical penile prosthesis including:
an inflatable cylinder at its distal end;
an endcap at its proximal end; and
a fill tube for fluid to inflate the cylinder.

3. The system of claim 1, wherein the joint further comprises:
a small, thin baseplate including edges and having a channel cut down the center of the baseplate; and
a drilled and tapped sliding edge clamp mounting hole placed through opposing baseplate edges, above and parallel to the channel; and
wherein the at least one receptacle mounting hole is placed in the baseplate.

4. The system of claim 1, wherein the sliding edge clamp comprises:
a base hook having an open part; and
a sliding hook including open part facing the open part of the base hook;
wherein the distance between the sliding hook and base hook is adjustable to accommodate different sized patients.

5. The system of claim 4, wherein the base hook comprises:
a leading edge attached over the channel of the joint, thereby forming a slot for the sliding hook to enter;
a second edge which may be bent at 90 degrees to the leading edge; and
a trailing edge which may be bent at 120 degrees to the second edge.

6. The system of claim 5, wherein the sliding hook hooks over an edge or side of the bone, the sliding hook having a leading edge, at least as long as the bone's width, configured to enter the slot and extend into the slot's void, a short edge which may be bent at 90 degrees to the leading edge, and a curved extension to the small edge whose radius is sized to hook over an edge or side of a bone.

7. The system of claim 6, wherein the sliding edge clamp further comprises:
a tightening system including:
a tab on the sliding hook attached at the outside of the small edge, the tab having a drill hole in the middle to match a sliding edge clamp mounting hole in the joint; and
a machine screw at least as long as the leading edge of the sliding hook, wherein the machine screw is configured to pass through the hole in the tab and be screwed and tightened into the joint's sliding edge clamp mounting hole.

8. The system of claim 2, wherein the receptacle comprises:
a one-piece pipe clip for clamping the endcap of the cylindrical prosthesis to the joint, the one-piece clip including:
a mounting screw;
a cylindrical tube section having a radius that is smaller than the radius of the cylindrical prosthesis;
a bottom hole drilled in the bottom of the cylindrical tube section;
a coupling rotating in at least one plane between the receptacle and the joint formed by the mounting screw or rivet passing through the bottom hole and attached to the joint.

9. The system of claim 2, wherein the receptacle comprises a socket clamp for clamping the endcap of the cylindrical prosthesis to the joint, the socket clamp including:
a thin walled pipe or truncated cone having an inside size and shape that matches the outside size and shape of the endcap;
a mounting hole drilled in the pipe bottom; and
a coupling rotating in at least one plane between the receptacle and the joint formed by a screw or rivet passing through the mounting hole and attached to the joint.

10. The system of claim 2, wherein the receptacle comprises a pin clamp for clamping the endcap of a cylindrical prosthesis to the joint, the pin clamp including:
  a hole drilled in an endcap of the cylindrical prosthesis;
  a washer comprising a thin-walled pipe section and a mounting hole drilled in the washer; and
  a coupling rotating in at least one plane between the receptacle and the joint formed by a screw or rivet passing through the mounting hole and prosthesis endcap and attached to the joint.

11. The system of claim 2, wherein the receptacle comprises an ear clamp for clamping the endcap of a cylindrical prosthesis to the joint, the ear clamp including:
  a thin cylindrical pipe with at least one rectangular portion protruding from at least one side of the pipe;
  a mounting hole drilled in the pipe bottom; and
  a coupling rotating in at least one plane between the receptacle and the joint formed by a screw or rivet passing through the mounting hole and attached to the joint.

12. The system of claim 2, wherein the receptacle comprises a slotted O-clip for clamping the endcap of the cylindrical prosthesis to the joint, the O-clamp including:
  a coiled band with an outside end overlapping an inside end;
  a mounting hole drilled in the center of the coiled band;
  a slot hook placed at one side of the outside end wherein the slot hook is used to tighten the coiled band around the endcap;
  multiple slots placed in the band and running from the mounting hole to the inside end wherein the slots receive the slot hook to tighten the coiled band around the endcap;
  a tab placed at the outside end and on the opposing side to the slot hook wherein a tool is placed in the tab and a slot and squeezed to tighten the coiled band around the endcap;
  a coupling rotating in at least one plane between the receptacle and the joint formed by a screw or rivet passing through the mounting hole and attached to the joint.

13. The system of claim 1, wherein the receptacle and sliding edge clamp are constructed of MRI-safe materials including stainless steel, titanium, zirconia, polyetheretherketone (PEEK) or combinations thereof.

14. The system of claim 1, wherein the sliding edge clamp is comprised of semi-ridged material that when tightened against the bone may slightly deform thereby conforming to the bone contours.

15. The system of claim 1, wherein the sliding edge clamp couples to the receptacle, with the receptacle extending outwardly from the sliding edge clamp and positioned to receive the endcap of the prosthesis.

16. A system for anchoring an inflatable penile prosthesis cylinder to an inferior ramus of the ischium of a patient, the system comprising:
  a sliding edge clamp extending about and coupling to the inferior ramus of the ischium, the clamp comprising:
  a base hook and joint extending about at least a portion of the inferior ramus of the ischium; and
  a sliding hook extending about at least a portion of the inferior ramus of the ischium, the sliding hook coupling to the joint;
  a penile prosthesis having a proximal end and a distal end, the proximal end including an endcap; and
  a receptacle coupled to the joint, the receptacle positioned to receive the endcap of the prosthesis and align the prosthesis with the patient's anatomy.

17. A method for surgically installing prostheses, the method comprising:
  making an opening incision in a patient;
  exposing ischiopubic rami of the patient;
  positioning a sliding edge clamp about a medial inferior ramus of the ischium, wherein the sliding edge clamp is comprised of a base hook attached to a joint, the joint having at least one receptacle mounting hole, and a sliding hook;
  installing the prosthesis in a receptacle, the receptacle attached to the joint; and
  securing the sliding edge clamp.

18. The method of claim 17, wherein positioning the sliding edge clamp comprises:
  arranging the sliding edge clamp around at least a portion of the medial inferior ramus of the ischium, the base hook including a first portion that substantially conforms to the posterior edge of the inferior ramus of the ischium;
  arranging a sliding hook around at least a portion of the anterior edge of the inferior ramus of the ischium, the sliding hook including a curved portion that substantially conforms to the anterior inferior ramus of the ischium;
  arranging the receptacle parallel to the medial ischiopubic ramus, and
  tightening the sliding edge clamp about the medial inferior ramus of the ischium with a screw.

19. The method of claim 17, further comprising aligning the prosthesis with the ischiopubic ramus by finding the correct position of the prosthesis with regard to the ischiopubic ramus and aligning the receptacle accordingly; and
  securing the prosthesis by inserting the prosthesis in the receptacle.

20. The method of claim 17, further comprising placing uncured padding between the sliding edge clamp and a bone of the patient and allowing the padding to cure after the sliding edge clamp is tightened in place.

* * * * *